(12) United States Patent
Slivka et al.

(10) Patent No.: US 8,034,085 B2
(45) Date of Patent: Oct. 11, 2011

(54) NON-FUSION SPINAL CORRECTION SYSTEMS AND METHODS

(75) Inventors: Michael A. Slivka, Taunton, MA (US); Hassan A. Serhan, S. Easton, MA (US)

(73) Assignee: DePuy Spine, Inc., Raynham, MA (US)

( * ) Notice: Subject to any disclaimer, the term of this patent is extended or adjusted under 35 U.S.C. 154(b) by 1149 days.

(21) Appl. No.: 10/709,796

(22) Filed: May 28, 2004

(65) Prior Publication Data

US 2005/0277920 A1 Dec. 15, 2005

(51) Int. Cl.
*A61B 17/70* (2006.01)

(52) U.S. Cl. .................. 606/266; 606/270; 606/277

(58) Field of Classification Search .......... 606/61, 606/280, 70–71, 286–291, 295, 297, 54–59, 606/324; 403/389, 391
See application file for complete search history.

(56) References Cited

U.S. PATENT DOCUMENTS

| | | | | |
|---|---|---|---|---|
| 3,997,138 A | * | 12/1976 | Crock et al. | 248/67.5 |
| 4,620,533 A | * | 11/1986 | Mears | 606/54 |
| 4,648,388 A | * | 3/1987 | Steffee | 606/261 |
| 4,653,481 A | * | 3/1987 | Howland et al. | 606/261 |
| 4,773,402 A | * | 9/1988 | Asher et al. | 606/250 |
| 5,092,866 A | | 3/1992 | Breard et al. | |
| 5,282,863 A | | 2/1994 | Burton | |
| 5,330,473 A | * | 7/1994 | Howland | 606/61 |
| 5,387,213 A | | 2/1995 | Breard et al. | |
| 5,395,374 A | | 3/1995 | Miller et al. | |
| 5,397,363 A | | 3/1995 | Gelbard | |
| 5,417,690 A | | 5/1995 | Sennett et al. | |
| 5,582,612 A | * | 12/1996 | Lin | 606/250 |
| 5,613,968 A | * | 3/1997 | Lin | 606/320 |
| 5,620,443 A | * | 4/1997 | Gertzbein et al. | 606/252 |
| 5,702,395 A | * | 12/1997 | Hopf | 606/61 |
| 5,704,936 A | | 1/1998 | Mazel | |
| 5,725,582 A | | 3/1998 | Bevan et al. | |
| 5,766,254 A | | 6/1998 | Gelbard | |
| 5,782,831 A | | 7/1998 | Sherman | |
| 5,810,817 A | * | 9/1998 | Roussouly et al. | 606/250 |
| RE36,221 E | | 6/1999 | Breard et al. | |
| 5,951,553 A | | 9/1999 | Betz | |
| 5,964,769 A | * | 10/1999 | Wagner et al. | 606/74 |

(Continued)

FOREIGN PATENT DOCUMENTS

EP 669109 A1 8/1995

(Continued)

OTHER PUBLICATIONS

Piggott Harry, "Growth Modification in the Treatment of Scoliosis", Orthopedics, vol. 10/No. 6, pp. 945-952 (Jun. 1987).

(Continued)

*Primary Examiner* — Eduardo C Robert
*Assistant Examiner* — Mary Hoffman
(74) *Attorney, Agent, or Firm* — Nutter McClennen & Fish LLP

(57) ABSTRACT

Methods and devices that utilize segmental fixation between several adjacent vertebrae, thus allowing each vertebra to be adjusted independently, are provided. In general, the device includes a spinal anchoring element that is adapted to seat at least one spinal fixation element, and a closure mechanism that is adapted to mate to the spinal anchoring element to lock the at least one spinal fixation element in a fixed position relative to the spinal anchoring element.

20 Claims, 12 Drawing Sheets

U.S. PATENT DOCUMENTS

| | | | |
|---|---|---|---|
| 6,066,140 A * | 5/2000 | Gertzbein et al. | 606/250 |
| 6,083,224 A * | 7/2000 | Gertzbein et al. | 606/250 |
| 6,106,527 A * | 8/2000 | Wu et al. | 606/250 |
| 6,132,431 A | 10/2000 | Nilsson et al. | |
| 6,136,000 A * | 10/2000 | Louis et al. | 606/250 |
| 6,136,002 A * | 10/2000 | Shih et al. | 606/61 |
| 6,206,879 B1 * | 3/2001 | Marnay et al. | 606/53 |
| 6,248,106 B1 | 6/2001 | Ferree | |
| 6,254,603 B1 * | 7/2001 | Gertzbein et al. | 606/250 |
| 6,287,308 B1 | 9/2001 | Betz | |
| 6,296,643 B1 | 10/2001 | Hopf | |
| 6,299,613 B1 | 10/2001 | Ogilvie | |
| 6,325,805 B1 | 12/2001 | Ogilvie | |
| 6,361,535 B2 | 3/2002 | Jackson | |
| 6,391,030 B1 | 5/2002 | Wagner et al. | |
| 6,423,065 B2 | 7/2002 | Ferree | |
| 6,436,099 B1 | 8/2002 | Drewry | |
| 6,471,704 B2 * | 10/2002 | Gertzbein et al. | 606/250 |
| 6,551,320 B2 | 4/2003 | Lieberman | |
| 6,602,254 B2 * | 8/2003 | Gertzbein et al. | 606/250 |
| 6,610,063 B2 * | 8/2003 | Kumar et al. | 606/250 |
| 6,616,669 B2 | 9/2003 | Ogilvie | |
| 6,623,484 B2 | 9/2003 | Betz | |
| 6,626,906 B1 * | 9/2003 | Young | 606/278 |
| 6,702,817 B2 * | 3/2004 | Beger et al. | 606/86 B |
| 6,749,612 B1 * | 6/2004 | Conchy et al. | 606/250 |
| 6,783,527 B2 | 8/2004 | Drewry | |
| 6,884,241 B2 | 4/2005 | Bertranou et al. | |
| 6,953,462 B2 | 10/2005 | Lieberman | |
| 7,008,423 B2 * | 3/2006 | Assaker et al. | 606/61 |
| 7,008,426 B2 | 3/2006 | Paul | |
| 7,118,571 B2 * | 10/2006 | Kumar et al. | 606/278 |
| 7,137,983 B2 | 11/2006 | Farkas et al. | |
| 7,166,108 B2 * | 1/2007 | Mazda et al. | 606/305 |
| 7,172,600 B2 * | 2/2007 | Beger et al. | 606/104 |
| 7,211,087 B2 * | 5/2007 | Young | 606/278 |
| 7,344,537 B1 * | 3/2008 | Mueller | 606/278 |
| 7,367,978 B2 | 5/2008 | Drewry et al. | |
| 2001/0010000 A1 * | 7/2001 | Gertzbein et al. | 606/61 |
| 2002/0019636 A1 | 2/2002 | Ogilvie | |
| 2002/0035365 A1 * | 3/2002 | Kumar et al. | 606/61 |
| 2002/0035366 A1 | 3/2002 | Walder et al. | |
| 2002/0042615 A1 | 4/2002 | Graf et al. | |
| 2002/0143329 A1 | 10/2002 | Serhan et al. | |
| 2003/0083657 A1 | 5/2003 | Drewry | |
| 2004/0106921 A1 | 6/2004 | Cheung | |
| 2004/0172025 A1 | 9/2004 | Drewry | |
| 2005/0010220 A1 | 1/2005 | Casutt et al. | |
| 2005/0154388 A1 * | 7/2005 | Roussouly et al. | 606/61 |
| 2005/0171537 A1 * | 8/2005 | Mazel et al. | 606/61 |
| 2005/0277920 A1 * | 12/2005 | Slivka et al. | 606/61 |
| 2005/0277922 A1 | 12/2005 | Trieu et al. | |
| 2006/0079892 A1 * | 4/2006 | Roychowdhury et al. | 606/61 |
| 2006/0122599 A1 | 6/2006 | Drewry et al. | |
| 2006/0149231 A1 * | 7/2006 | Bray | 606/61 |
| 2006/0149242 A1 | 7/2006 | Kraus et al. | |
| 2007/0123860 A1 * | 5/2007 | Francis et al. | 606/61 |
| 2007/0123864 A1 | 5/2007 | Walder et al. | |
| 2007/0173817 A1 * | 7/2007 | Sournac et al. | 606/61 |
| 2007/0233075 A1 | 10/2007 | Dawson | |
| 2008/0065114 A1 | 3/2008 | Stone et al. | |
| 2008/0140122 A1 | 6/2008 | Bethell | |
| 2008/0140123 A1 | 6/2008 | Ferree | |
| 2008/0140133 A1 | 6/2008 | Allard et al. | |
| 2008/0161854 A1 | 7/2008 | Bae et al. | |
| 2008/0234679 A1 | 9/2008 | Sarin et al. | |
| 2008/0262546 A1 | 10/2008 | Calvosa et al. | |
| 2008/0262550 A1 | 10/2008 | Ferree | |
| 2008/0294198 A1 | 11/2008 | Jackson | |
| 2008/0300599 A1 | 12/2008 | Anapliotis et al. | |
| 2008/0312695 A1 | 12/2008 | Sybert et al. | |
| 2008/0319487 A1 | 12/2008 | Fielding et al. | |
| 2009/0018662 A1 | 1/2009 | Pasquet et al. | |
| 2009/0054902 A1 | 2/2009 | Mickiewicz et al. | |

FOREIGN PATENT DOCUMENTS

| | | |
|---|---|---|
| WO | 9320771 A1 | 10/1993 |
| WO | WO-93/22989 A1 | 11/1993 |
| WO | 9614022 A1 | 5/1996 |
| WO | 9944527 A1 | 9/1999 |
| WO | WO-01/03570 A2 | 1/2001 |
| WO | 02102259 A2 | 12/2002 |
| WO | 03003901 A2 | 1/2003 |
| WO | 2006105935 A1 | 10/2006 |
| WO | 2006136937 A2 | 12/2006 |
| WO | 2007060534 A2 | 5/2007 |

OTHER PUBLICATIONS

Dwyer, A. F. "Experience of Anterior Correction of Scoliosis" Anterior Correction of Scoliosis, No. 93, pp. 191-206 (Jun. 1973).

Dwyer, A. F., et al. "Anterior Approach to Scoliosis" The Journal of Bone and Joint Surgery, vol. 56B, No. 2, pp. 218-224 (May 1974).

Betz, Randal R., et al. "An Innovative Technique of Vertebral Body Stapling for the Treatment of Patients With Adolescent Idiopathic Scoliosis: A Feasibility, Safety, and Utility Study" . SPINE, vol. 28, No. 205, pp. S255-S265 (2003).

\* cited by examiner

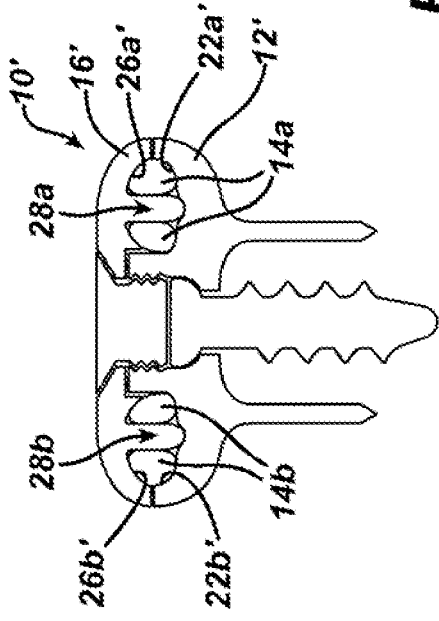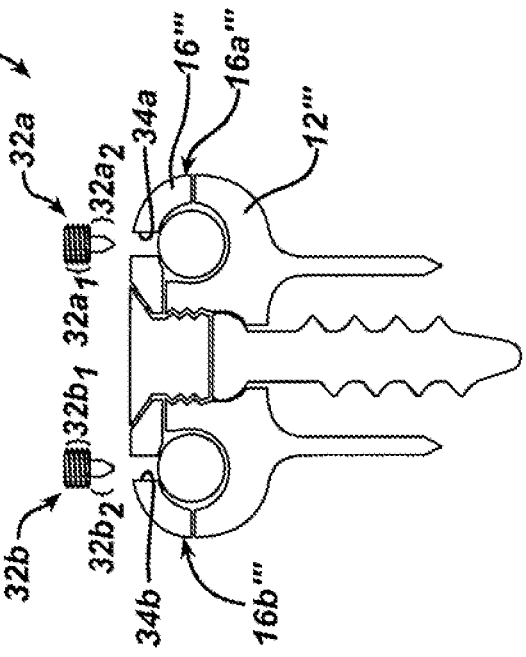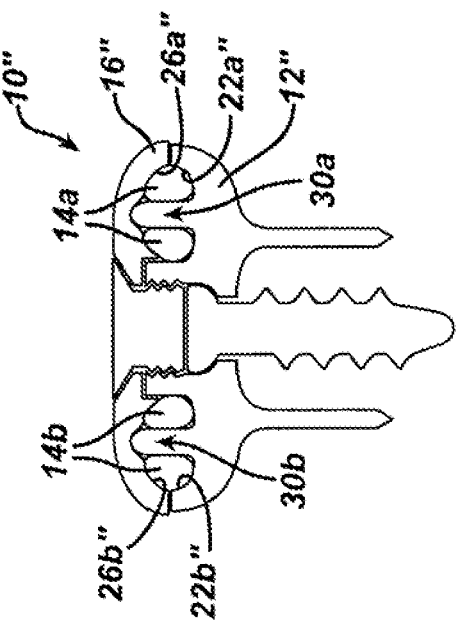

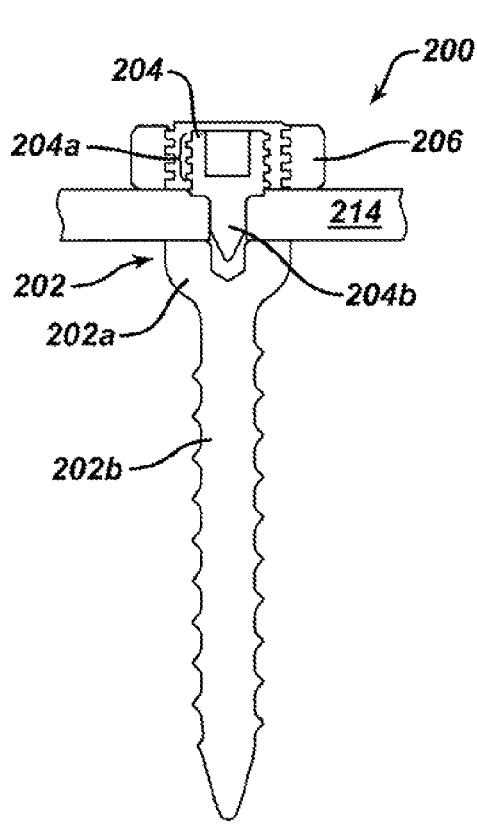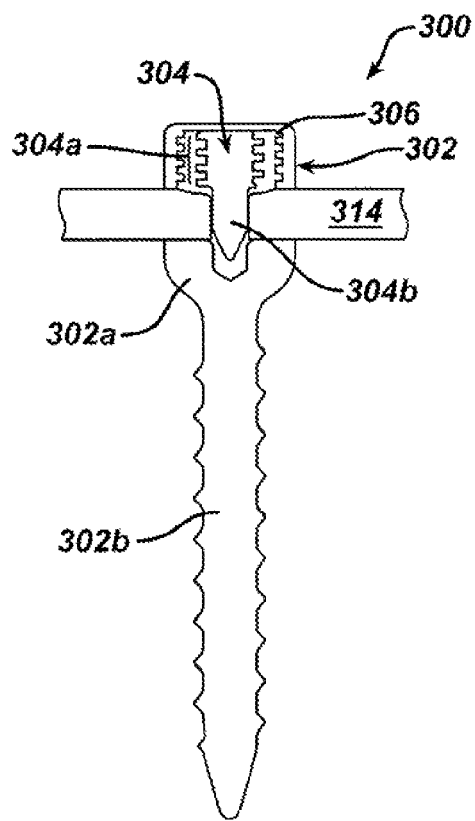

NON-FUSION SPINAL CORRECTION
SYSTEMS AND METHODS

FIELD OF THE INVENTION

The present invention relates to non-fusion methods and devices for correcting spinal deformities.

BACKGROUND OF THE INVENTION

Spinal deformities, which include rotation, angulation, and/or curvature of the spine, can result from various disorders, including, for example, scoliosis (abnormal curvature in the coronal plane of the spine), kyphosis (backward curvature of the spine), and spondylolisthesis (forward displacement of a lumbar vertebra). Early techniques for correcting such deformities utilized external devices that apply force to the spine in an attempt to reposition the vertebrae. These devices, however, resulted in severe restriction and in some cases immobility of the patient. Thus, to avoid this need, several rod-based techniques were developed to span across multiple vertebrae and force the vertebrae into a desired orientation.

In rod-based techniques, one or more rods are attached to the vertebrae at several fixation sites to progressively correct the spinal deformity. The rods are typically pre-curved to a desired adjusted spinal curvature. Wires can also be used to pull individual vertebra toward the rod. Once the spine has been substantially corrected, the procedure typically requires fusion of the instrumented spinal segments.

While several different rod-based systems have been developed, they tend to be cumbersome, requiring complicated surgical procedures with long operating times to achieve correction. Further, intraoperative adjustment of rod-based systems can be difficult and may result in loss of mechanical properties due to multiple bending operations. Lastly, the rigidity and permanence of rigid rod-based systems does not allow growth of the spine and generally requires fusion of many spine levels, drastically reducing the flexibility of the spine.

Accordingly, there remains a need for improved methods and devices for correcting spinal deformities, and in particular, there remains a need for non-fusion spinal correction systems and methods.

BRIEF SUMMARY OF THE INVENTION

The present invention provides methods and devices for treating spinal deformities. In general, the methods and devices utilize segmental fixation between several adjacent vertebrae, thus allowing each vertebrae to be repositioned independently. In one embodiment, a device is provided having a spinal anchoring element that is adapted to seat first and second spinal fixation elements at a distance spaced apart from one another, and a closure mechanism that is adapted to mate to the spinal anchoring element to lock each of the first and second spinal fixation elements in a fixed position relative to the spinal anchoring element. Each spinal fixation element can be, for example, a flexible fixation element that is preferably formed from a bioabsorbable material.

The spinal anchoring element can have a variety of configurations, but in an embodiment it includes a first recess that is adapted to receive a first spinal fixation element, and a second recess that is spaced a distance apart from the first recess and that is adapted to receive a second spinal fixation element. The first recess can be formed in a first end portion of the spinal anchoring element and the second recess can be formed in a second, opposed end portion of the spinal anchoring element, and each recess is preferably formed in a superior surface of the anchoring element. A central portion can be formed between the first and second recesses for receiving a fastening element for mating the anchoring element to bone. In an exemplary embodiment, the central portion includes a bore extending therethrough for receiving a fastening element, such as a bone screw.

The closure mechanism that mates to the anchoring element can also have a variety of configurations, but in an embodiment it includes a central portion that is adapted to receive a locking mechanism, such as a set screw, for mating the closure mechanism to the spinal anchoring element. The closure mechanism can also include a first end portion that is adapted to lock a spinal fixation element within the first recess, and a second end portion that is adapted to lock a spinal fixation element within the second recess. In one embodiment, the first and second ends portions on the closure mechanism can include a bore formed therethrough for receiving an engagement mechanism that is adapted to extend into and engage a spinal fixation element disposed within each of the first and second recesses in the spinal anchoring element. Each engagement mechanism can include, for example, a proximal, threaded portion that is adapted to mate with corresponding threads formed within the bore in the closure mechanism, and a distal pin member that is adapted to extend into a spinal fixation element positioned in each of the first and second recesses in the anchoring element. In another embodiment, the closure mechanism can include at least one protrusion formed thereon and adapted to extend into and engage a spinal fixation element disposed in each of the first and second recesses formed in the spinal anchoring element.

In yet another embodiment, the device can include a bone engaging member extending distally from the inferior surface of each of the first and second end portions of the anchoring element. The bone engaging member can be, for example, a spike that is adapted to extend into bone to prevent rotation of the spinal anchoring element.

The present invention also provides a medical system for treating spinal deformities that includes first and second flexible spinal fixation elements, and several spinal anchoring devices. Each anchoring device is adapted to mate to a vertebra and to engage each of the first and second spinal fixation elements such that the first and second spinal fixation elements can be tensioned between each spinal anchoring device to adjust a position of each vertebra in both a sagittal plane and a coronal plate when the spinal anchoring devices are implanted in several adjacent vertebrae. The system can also include several closure mechanisms that are adapted to mate to the spinal anchoring elements to lock the first and second flexible spinal fixation elements therein.

In other aspects of the invention, a non-fusion spinal anchoring device for treating spinal deformities is provided having an anchoring element that is adapted to seat an elongate element, such as a flexible fixation element, and an engagement mechanism that is adapted to mate to the anchoring element. The engagement mechanism includes at least one protrusion formed thereon for extending into and engaging an elongate element disposed within the anchoring element to prevent sliding movement of the elongate element relative to the anchoring element. In an exemplary embodiment, the engagement mechanism includes a proximal threaded portion that is adapted to mate with corresponding threads formed on the anchoring element. The protrusion(s) preferably extends distally from the proximal threaded portion.

Methods for correcting spinal deformities are also provided. In one embodiment, the method includes the steps of implanting an anchoring device within each of a plurality of adjacent vertebrae in a spinal column, coupling first and second elongate elements to each anchoring device such that the first and second elongate elements are spaced a distance apart from one another, and locking the first and second elongate elements relative to each anchoring device to selectively tension the first and second elongate elements between each anchoring device, thereby adjusting a position of the plurality of adjacent vertebrae in the spinal column relative to one another. The vertebrae are preferably adjusted along both a sagittal plane and a coronal plane of a patient's body.

In another non-fusion method for correcting spinal deformities, a spinal anchoring device is implanted in each of a plurality of vertebrae, and first and second flexible fixation elements are fixedly coupled to each spinal anchoring device such that segmental tension is applied between each anchoring device to adjust a position of each of the plurality of vertebrae in both a coronal plane and a sagittal plane of a patient's body. Each anchoring device can include an anchoring element that is adapted to mate to a vertebra, and a closure mechanism that is adapted to lock each of the first and second flexible fixation elements in a fixed position relative to the anchoring element.

BRIEF DESCRIPTION OF THE DRAWINGS

The invention will be more fully understood from the following detailed description taken in conjunction with the accompanying drawings, in which:

FIG. 2A is a side, cross-sectional view of an alternative embodiment of the spinal anchoring device shown in FIG. 1;

FIG. 2B is a side, cross-sectional view of another alternative embodiment of the spinal anchoring device shown in FIG. 1;

FIG. 2C is a side, cross-sectional view of yet another alternative embodiment of the spinal anchoring device shown in FIG. 1;

FIG. 5 is a cross-sectional view of yet another embodiment of a spinal anchoring device having inner and outer locking mechanisms;

FIG. 6 is a cross-sectional view of another embodiment of a spinal anchoring device having two inner locking mechanisms;

DETAILED DESCRIPTION OF THE INVENTION

The present invention provides methods and devices for treating spinal deformities, and in particular to non-fusion methods and devices for treating spinal deformities. In general, the methods and devices utilize segmental fixation between several adjacent vertebrae, thus allowing each vertebrae to be adjusted independently. The vertebrae can be individually adjusted along both the coronal plane and the sagittal plane of the patient's body. Such a technique can be advantageous for shortening and/or halting growth of the patient's spine, however the methods and devices can be used in a variety of other spinal applications. By way of non-limiting example, the device can be used for posterior dynamization to function as a decompressive device for stenosis and/or an adjunct to an intervertebral disc to unload the facets of the vertebra.

Figure 1:
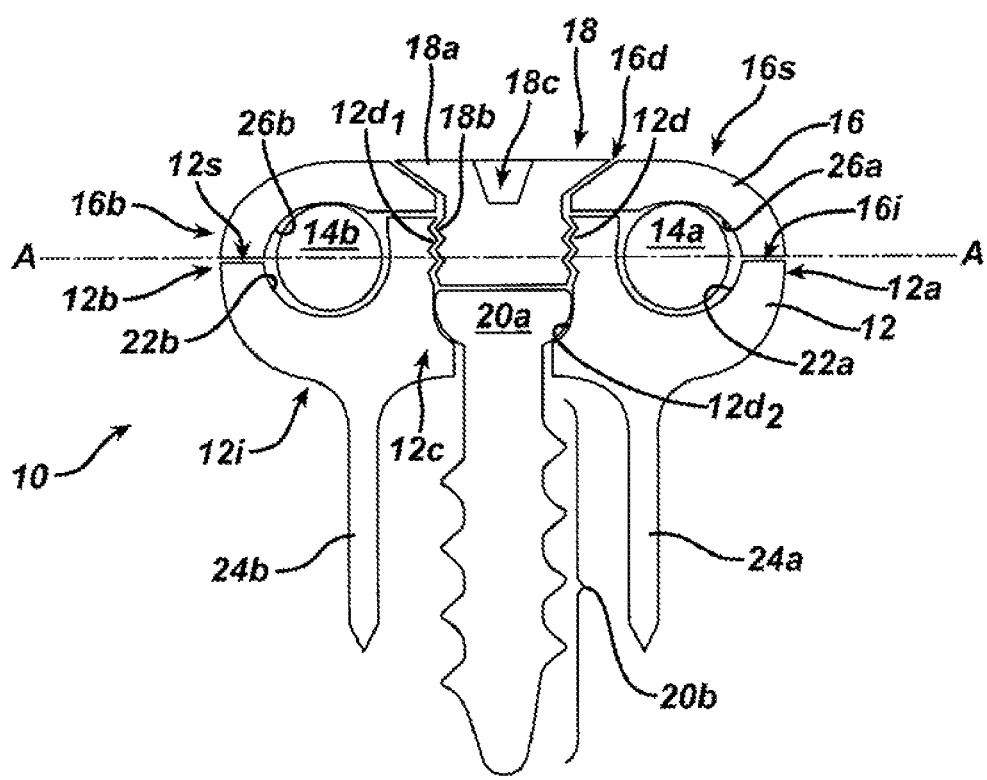
FIG. 1 is perspective view illustration of one embodiment of a spinal anchoring device in accordance with the present invention.

FIG. 1 illustrates one embodiment of a spinal anchoring device 10 in accordance with the present invention. As shown, the spinal anchoring device 10 includes a spinal anchoring element 12 that is adapted to seat first and second spinal fixation elements 14a, 14b at a distance spaced apart from one another, and a closure mechanism 16 that is adapted to mate to the spinal anchoring element 12 to lock each of the first and second spinal fixation elements 14a, 14b in a fixed position relative to the spinal anchoring element 12. The device 10 can also include a fastening element 20 for mating the spinal anchoring element 12 to bone, and a locking mechanism 18 for mating the closure mechanism 16 to the spinal anchoring element 12. While not illustrated, a single fastening element can be used to attach the anchoring element to bone and to lock the closure mechanism to the anchoring element.

A person skilled in the art will appreciate that the spinal anchoring device 10 can be used with a variety of spinal fixation elements, and by way of non-limiting example, suitable fixation elements include rigid or flexible spinal rods, cables, tethers, wires, etc. The fixation elements can also be formed from a variety of materials, including, for example, stainless steel, titanium, non-absorbable polymeric braided materials, such as ultra-high molecular weight polyethylene or poly(ethylene terephthalate), absorbable polymeric braided materials, such as poly(L-lactic acid) or other high strength, slowly degrading polymers known in the art.

The spinal anchoring element 12 can have a variety of configurations, but, as stated above, it should be adapted to seat first and second spinal fixation elements 14a, 14b therein. In an exemplary embodiment, as shown, the anchoring element 12 is in the form of a generally elongate housing having opposed superior and inferior surfaces 12s, 12i, and opposed first and second ends 12a, 12b. The inferior surface 12i is adapted to be positioned against bone when the spinal anchoring element 12 is implanted, and the superior surface 12s is adapted to seat the first and second fixation elements 14a, 14b. Accordingly, the superior surface 12s can include first and second opposed recesses 22a, 22b formed therein adjacent the opposed first and second ends 12a, 12b thereof for seating the spinal fixation elements 14a, 14b. The recesses 22a, 22b are spaced a distance apart from one another to allow the fixation elements 14a, 14b to be positioned at different locations along the patient's spinal column, as will be discussed in more detail below. Each recess 22a, 22b can vary in shape and size depending on the configuration of the fixation element 14a, 14b being disposed therein, but in an exemplary embodiment each recess 22a, 22b has a substantially convex shape. The recesses 22a, 22b also preferably extend across the superior surface 12s of the anchoring element 12 in a direction that is substantially transverse to an axis L that extends between the first and second ends 12a, 12b. As a result, the spinal fixation elements 14a, 14b will extend in the same direction as the recesses 12a, 12b.

The spinal anchoring element 12 also preferably includes a central portion 12c that is formed between the opposed ends 12a, 12b and that is adapted to receive a fastening element 20 for mating the spinal anchoring element 12 to bone. While other techniques can be used to mate the anchoring element 12 to bone, and the anchoring element 12 can be mated at other locations on the device 10, in an exemplary embodiment the central portion 12c includes a central pathway or bore 12d extending therethrough for receiving the fastening element 20. The central bore 12d can vary in shape and size depending on the configuration of the fastening element 20. However, in an exemplary embodiment, the fastening element 20 is a bone screw having a head 20a and a threaded shank 20b, and the bore 12d includes a distal portion or recess $12d_2$ that is adapted to seat the head 20a of the bone screw 20 such the shank 20b of the bone screw 20 extends through the bore 12d. In other words, the bone screw 20 can be polyaxial relative to the anchoring element 12. In use, the bone screw 20 can be inserted through the bore 12d and threaded into bone, thereby attaching the anchoring element 12 to bone. A person skilled in the art will appreciate that, while a polyaxial bone screw 20 is shown, the bone screw 20 can be monoaxial or it can have a variety of other configurations. Other techniques for attaching the anchoring element 12 to bone may also be used.

The spinal anchoring element 12 can also optionally include one or more bone-engaging members formed thereon and adapted to prevent rotational movement of the anchoring element 12 when the anchoring element 12 is implanted. FIG. 1 illustrates one exemplary embodiment of first and second bone-engaging members 24a, 24b formed on and extending distally from the inferior surface 12i of the anchoring element 12 at a location adjacent to the first and second ends 12a, 12b of the anchoring element 12. The bone-engaging members 24a, 24b are in the form of spikes that are adapted to extend into bone, however they can have a variety of other shapes. In use, a mallet or other device can be used to apply a force to the anchoring element 12 to impact the spikes 24a, 24b into bone at the desired implant site. The fastening element, e.g., bone screw 20, can then be inserted through the central bore 12d and threaded into bone to further secure the anchoring element 12 to the bone.

Still referring to FIG. 1, the device 10 also includes a closure mechanism 16 that is adapted to mate to the spinal anchoring element 12 to lock each of the first and second spinal fixation elements 14a, 14b in a fixed position relative to the spinal anchoring element 12. The configuration of the closure mechanism 16 can vary, and it can be formed from separate components, but more preferably it is formed from a single elongate member having a shape that is substantially similar to the shape of the anchoring element 12. As shown in FIG. 1, the closure mechanism 16 includes first and second opposed ends 16a, 16b that are configured to be juxtapositioned on the first and second opposed ends 12a, 12b of the anchoring element 12. The closure mechanism 16 also includes superior and inferior surfaces 16s, 16i. The inferior surface 16i, which is the surface that faces the superior surface 12s of the anchoring element 12, is adapted to lock the first and second fixation elements 14a, 14b within the recesses 22a, 22b formed in the anchoring element 12. Accordingly, the inferior surface 16i can include first and second recesses 26a, 26b formed therein and opposed to the first and second recesses 22a, 22b in the anchoring element 12 to facilitate engagement of the fixation elements 14a, 14b. While the shape of each recess 26a, 26b will vary depending on the shape of each fixation element 14a, 14b, in an exemplary embodiment each recess 26a, 26b preferably has a substantially concave shape such that the opposed recesses 22a, 26a, 22b, 26b in the anchoring element 12 and the closure mechanism 16 form a substantially cylindrical cavity extending therebetween for receiving substantially cylindrical, elongate fixation elements 14a, 14b. Each recess 26a, 26b should also extend in the same direction as the recesses 22a, 22b formed in the anchoring element 12.

The closure mechanism 16 can be mated to the spinal anchoring element 12 using a variety of techniques, but in an exemplary embodiment, as shown, the closure mechanism 16 includes a central portion 16c having a central bore 16d extending therethrough for receiving a locking mechanism 18. The central bore 16d is preferably axially aligned with the central bore 12d in the anchoring element 12 to allow the locking mechanism 18 to extend through the closure mechanism 16 and to engage the anchoring element 12. While various types of locking mechanisms can be used, in an exemplary embodiment the locking mechanism 18 is a set screw 18 having a head 18a and a threaded shank 18b. The bore 16d in the closure mechanism 16 is therefore preferably adapted to seat the head 18a of the set screw, yet to allow the threaded shank 18b to pass therethrough. The bore 16d can optionally be tapered from the superior surface 16s to the inferior surface 16i to further facilitate positioning of the head 18a of the set screw 18 therein, and more preferably to allow the head 18a to seat flush or sub-flush with the superior surface 16s of the closure mechanism 16. When the head 18a is seated within the bore 16d in the closure mechanism, the threaded shank 18b of the set screw 18 extends through the bore 16d to engage the anchoring element 12. The bore 12d in the anchoring element 12 is thus preferably adapted to mate with the threaded shank 18d to allow the set screw 18 to lock the closure mechanism 16 to the anchoring element 12, thereby locking the first and second fixation elements 14a, 14b within the recesses 22a, 22b, 26a, 26b in the closure mechanism 16 and anchoring element 12. As shown in FIG. 1, a proximal portion $12d_1$ of the bore 12d in the anchoring element 12 is threaded to mate with the threaded shank 18b of the set screw 18. A person skilled in the art will appreciate that a single fastening element can be used to lock the closure mechanism 16 to the anchoring element 12, and to also attach the anchoring element 12 to bone.

In use, when the set screw 18 is fully threaded into the bore 12d in the anchoring element 12, the closure mechanism 16 is locked to the anchoring element 12, thereby locking the first and second fixation elements 14a, 14b therebetween. Where the bone screw 20 is polyaxial, the shank 18b of the set screw 18 can be configured to contact the fastening element, e.g., bone screw 20, to lock the bone screw 20 in a fixed position relative to the anchoring element 12. In order to drive the set screw 18 into the anchoring element 12, the set screw 18 can include a mating element, such as a socket 18c, formed on or in the head 18a thereof for mating with or receiving a driver mechanism. A person skilled in the art will appreciate that a variety of other techniques can be used to lock the closure mechanism 16 to the anchoring element 12.

The spinal anchoring device 10 can also include a variety of engagement mechanisms that are adapted to engage the first and second fixation elements 14a, 14b to prevent slidable movement of the fixation elements 14a, 14b relative to the closure mechanism 16 and the anchoring element 12 when the closure mechanism 16 is locked to the anchoring element 12. FIGS. 2A-2C illustrate various embodiments of engagement mechanisms for use with the present invention. A person skilled in the art will appreciate that a variety of other techniques can be used to facilitate locking of the first and second fixation elements 14a, 14b within the device 10.

FIG. 2A illustrates one embodiment of a spinal anchoring device 10' having protrusions 28a, 28b formed within the first and second recesses 26a', 26b' of the closure mechanism 16', and FIG. 2B illustrates another embodiment of a spinal anchoring device 10" having protrusions 30a, 30b formed within the first and second recesses 22a", 22b" of the anchoring element 12'. The size and shape of the protrusions 28a, 28b, 30a, 30b can vary, but as shown each protrusion 28a, 28b, 30a, 30b can have a substantially triangular or spiked shape. In use, the protrusions 28a, 28b, 30a, 30b extend into the spinal fixation elements 14a, 14b to engage the spinal fixation elements 14a, 14b. For example, where each fixation element 14a, 14b is formed from a flexible cable or tether, the protrusions 28a, 28b, 30a, 30b will engage the fixation element to prevent it from sliding relative to the device 10', 10". A person skilled in the art will appreciate that the closure mechanism 16', 16" and/or the anchoring element 12', 12" can include any number of protrusions formed therein at any location.

FIG. 2C illustrates another embodiment of an engagement mechanism for preventing slidable movement of the fixation elements 14a, 14b within the device 10'". In this embodiment, the closure mechanism 16'" includes first and second bores 34a, 34b formed therein for receiving first and second engagement mechanisms 32a, 32b, each of which is adapted to engage the spinal fixation element 14a, 14b disposed between the closure mechanism 16'" and the anchoring element 12'". The bores 34a, 34b are preferably threaded, as shown, however they can be adapted to mate with the engagement mechanism 32a, 32b using a variety of other techniques, such as, for example, a snap-fit, an interference fit, etc. Each engagement mechanism 32a, 32b can also have a variety of configurations, but in an exemplary embodiment, as shown, each engagement mechanism 32a, 32b includes a proximal, threaded portion $32a_1$, $32b_1$ that is adapted to mate with the threaded bores 34a, 34b in the closure mechanism 16'", and a distal pin member $32a_2$, $32b_2$ that is adapted to extend into the spinal fixation element 14a, 14b positioned between the closure mechanism 16'" and the anchoring element 12'". While the distal pin member $32a_2$, $32b_2$ preferably extends into the fixation elements 14a, 14b, where a rigid fixation element is used, the distal pin member $32a_2$, $32b_2$ can use other techniques for engaging the fixation element 14a, 14b, such as an interference fit. The device 10'" can also include, in combination with the engagement mechanisms 32a, 32b, one or more protrusions (not shown) formed therein and adapted to extend into and/or engage the spinal fixation element 14a, 14b, such as those previously described with respect to FIGS. 2A-2B.

Figure 3A:
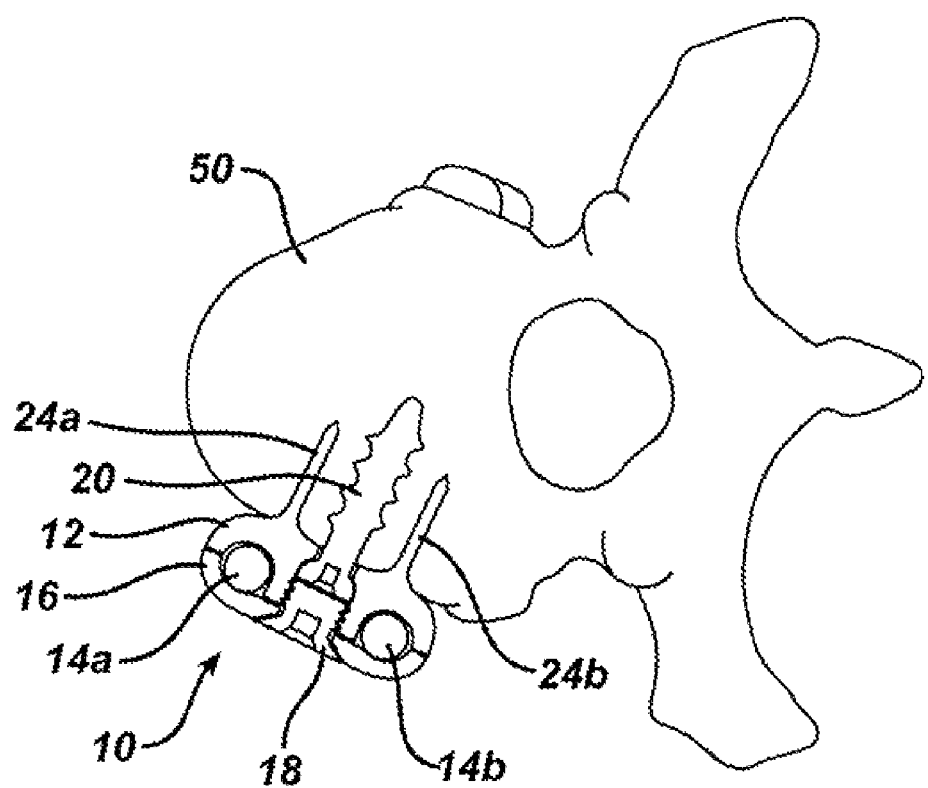
FIG. 3A is a cross-sectional view of the spinal anchoring device shown in FIG. 1 implanted in a vertebra.
Figure 3B:
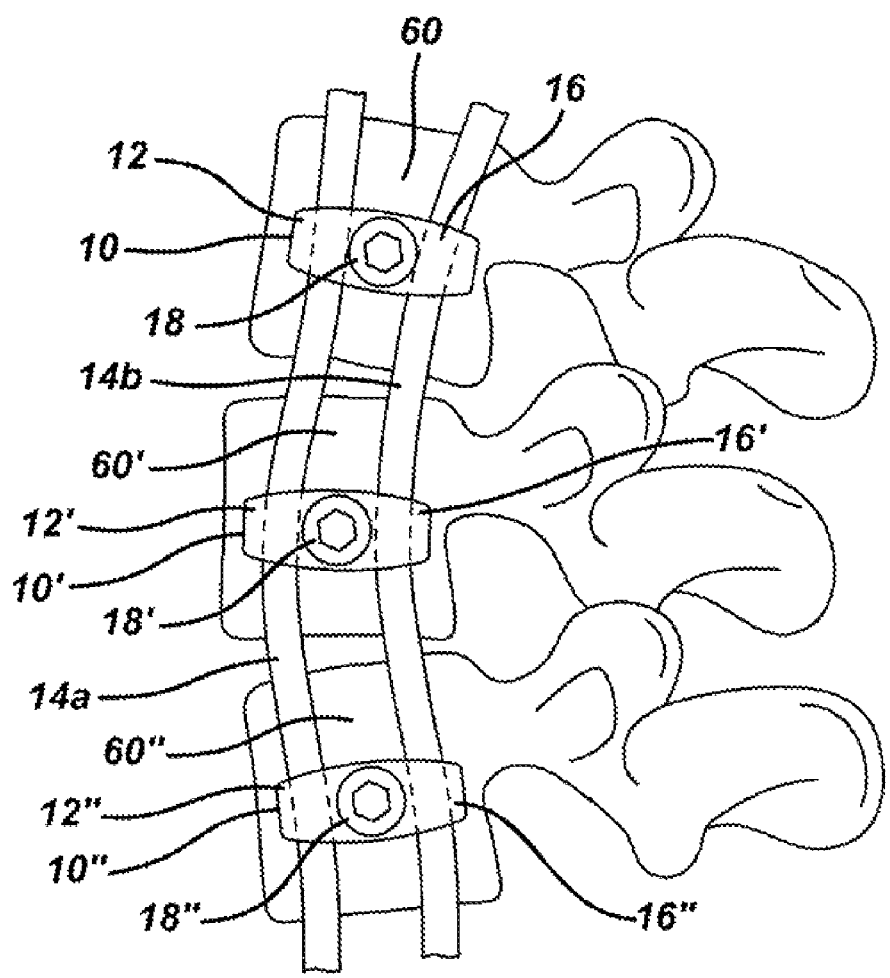
FIG. 3B is perspective view illustration of several spinal anchoring systems, as shown in FIG. 1, implanted along a portion of a human spinal column in accordance with another embodiment of the present invention.

FIGS. 3A-3B illustrate an exemplary method for correcting a spinal deformity. Referring to FIG. 3A, spinal anchoring device 10 (shown in FIG. 1) is shown in implanted in a patient's vertebra 60. The spinal anchoring element 12 is first implanted preferably by impacting the anchoring element 12 to insert the bone-engaging members or spikes 24a, 24b into the vertebra 60, thereby positioning the anchoring element 12 at the desired implant site. A fastening element, e.g., bone screw 20, can then be inserted through the bore 12d in the anchoring element 12 and threaded into the vertebra 60 to securely attach the anchoring element 12 to the vertebra 60. The position of the anchoring element 12 relative to the vertebra 60 can vary depending on the spinal deformity being corrected. In FIG. 3A, the anchoring element 12 is implanted in the lateral aspect of the vertebra 60.

As shown in FIG. 3B, once the anchoring element 12 is securely attached to the vertebra, several additional anchoring elements 12', 12" can be implanted within adjacent vertebrae 60', 60" along the patient's spine. The location of the anchoring elements 12, 12', 12" along the spine can vary depending on the deformity being corrected. First and second spinal fixation elements, such as fixation elements 14a, 14b, are then positioned with the recess in each anchoring element 12, 12', 12" such that the fixation elements 14a, 14b span across several vertebrae 60, 60', 60". A closure mechanism 16, 16', 16" can then be applied to each anchoring element 12, 12', 12" and a locking mechanism, e.g., set screw 18, 18', 18" can be loosely threaded to each anchoring element 12, 12', 12" to loosely attach the closure mechanisms 16, 16', 16" thereto. A tension of the fixation elements 14a, 14b between each device 10, 10', 10" can then be adjusted to apply a selected segmental tension, and the tension can be retained by tightening the locking mechanisms 16, 16', 16". The selected segmental tension can be configured to intraoperatively achieve correction immediately, or the tension can be configured such that the fixation elements 14a, 14b will asymmetrically restrict growth of the spine to achieve correction. Since the fixation elements 14a, 14b are spaced a distance apart from one another, and since the tension can be adjusted between each device 10, 10', 10", the fixation elements 14a, 14b can correct spinal deformities in both the sagittal plane and the coronal plane of the patient's body, i.e., the fixation elements 14a, 14b provide correction in all three rotational degrees of freedom.

Figure 4A:
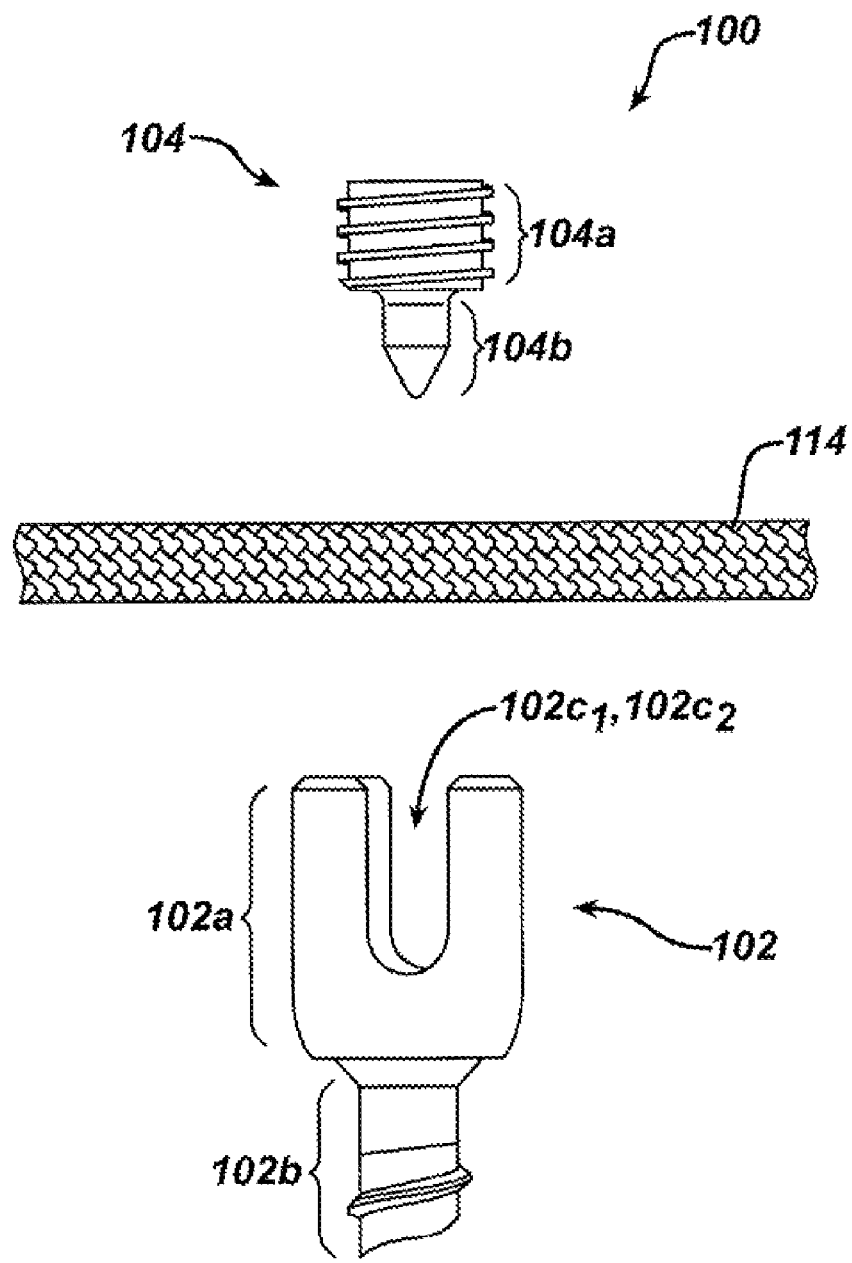
FIG. 4A is a side, disassembled view of another embodiment of a spinal anchoring device in accordance with the present invention.
Figure 4B:
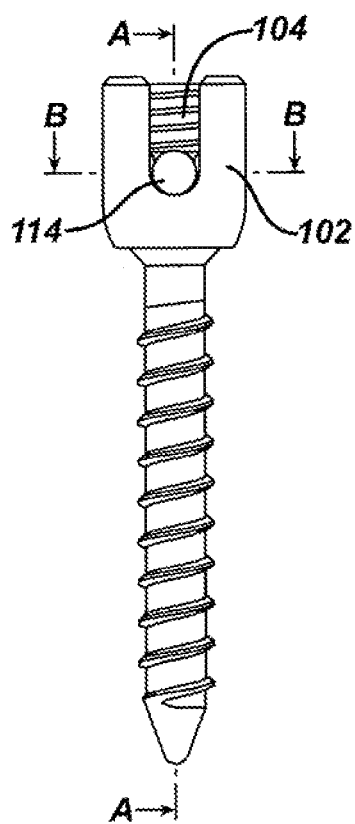
FIG. 4B is a side assembled view of the device shown in FIG. 4A.
Figure 4C:
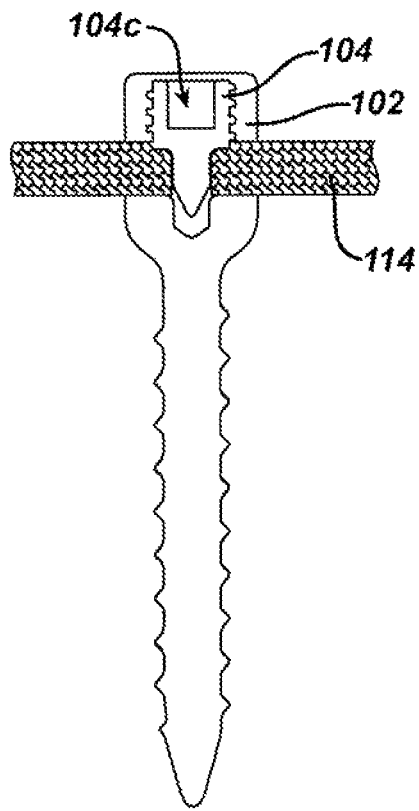
FIG. 4C is a cross-sectional view of the device shown in FIG. 4B taken across line A-A.
Figure 4D:
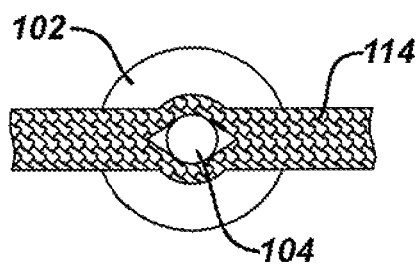
FIG. 4D is a cross-sectional view of the device shown in FIG. 4B taken across line B-B.

FIGS. 4A-4D illustrate yet another embodiment of a spinal anchoring device 100 in accordance with the present invention. The spinal anchoring device 100 is similar to spinal anchoring device 10, however it is preferably only adapted to seat a single spinal fixation element 114 therein. As shown in FIG. 4A, the device 100 generally includes an anchoring element 102 that is adapted to seat a fixation element 114, and an engagement mechanism 104 that is adapted to mate to the anchoring element 102 and to engage the fixation element 114 to lock the fixation element 114 within the anchoring element 102. In this embodiment, the device 100 is particularly adapted for use with a flexible fixation element 114. However, a person skilled in the art will appreciate that the device 100 can be modified for use with rigid fixation elements. In use, multiple spinal anchoring devices 100 can be implanted in each vertebra and/or in multiple adjacent vertebrae along a patient's spinal column to provide the desired correction in one or more rotational degrees of freedom.

The anchoring element 102 can have virtually any configuration, and it can be in the form of a spinal plate, a monoaxial bone screw, a polyaxial bone screw, a hook, or any other device known in the art for anchoring a spinal fixation element to bone. In the illustrated embodiment, the anchoring element 102 is a monoaxial bone screw having a threaded, bone engaging shank 102b that is coupled to a U-shaped head 102a. The head 102a include opposed recesses $102c_1$, $102c_2$ formed therein for receiving the fixation element 114. The head 102a also preferably includes threads (not shown), or some other mating element, formed therein for mating with threads, or some other complementary mating element, formed on the engagement mechanism 104.

The engagement mechanism 104 can also have a variety of configurations as long as it is adapted to mate to the anchoring element 102 to lock the fixation element 114 therein. As shown in FIG. 4A, the engagement mechanism 104 includes a proximal, threaded portion that is adapted to mate with corresponding threads formed within the U-shaped head 102a. As previously mentioned, other techniques can be used to mate the engagement mechanism 104 to the U-shaped head 102a, including, for example, a twist-lock closure mechanism, a snap-fit, etc. The engagement mechanism 104 also includes a distal portion 104b that extends distally from the proximal, threaded portion 104a and that is adapted to at least partially extend into the fixation element 114. As shown, the distal portion 104b is in the form of a pin or spike.

FIGS. 4A-4D illustrate the device 100 with the flexible fixation element 114 locked therein. As shown, the fixation element 114 is positioned to extend through the recesses $102c_1$, $102c_2$ in the U-shaped head 102a, and the engagement mechanism 104 is threaded into the head 102a to cause the distal pin 104b to penetrate through the fixation element 114. A driver device can be used to engage a mating element, such as a socket 104(c) (FIG. 4C), formed in the proximal threaded portion 104a of the engagement mechanism 104, and to rotate the engagement mechanism 104 to thread it into the anchoring element 102. Once the engagement mechanism 104 is fully threaded into the anchoring element 102, the fixation element 114 is locked in a fixed position such that it is prevented from moving relative to the anchoring element 102.

FIGS. 5 and 6 illustrate additional embodiments of engagement mechanisms for locking a fixation element within an anchoring element of a spinal fixation device. In the embodiment shown in FIG. 5, the spinal fixation device 200 includes inner and outer engagement mechanisms 204, 206. The inner engagement mechanism 204 is similar to engagement mechanism 104 shown in FIG. 4A as it includes a proximal threaded portion 204a that is adapted to mate with corresponding threads formed on an internal portion of the U-shaped head 202a of the anchoring element 202, and a distal portion 204b that extends distally from the proximal, threaded portion 204a and that is adapted to at least partially extend into a fixation element 214 seated within the anchoring element 202. The outer engagement mechanism 206 is also threaded and it is adapted to mate with corresponding threads formed on an outer portion of the U-shaped head 202a of the anchoring element 202. In use, the outer engagement mechanism 206 prevents the legs of the U-shaped head 202a from splaying, thereby further locking the spinal fixation element 214 within the U-shaped head 202a.

In the embodiment shown in FIG. 6, the spinal fixation device 300 includes two inner engagement mechanisms 304, 306. The first inner engagement mechanism 304 is similar to engagement mechanism 104 shown in FIG. 4A in that it includes a proximal threaded portion 304a and a distal portion 304b that is adapted to extend into a spinal fixation element 314 seated within the spinal anchoring element 302. The proximal threaded portion 304a does not, however, mate with the U-shaped head 302a of the anchoring element 302, but rather it mates with threads formed on an inner surface of the second inner engagement mechanism 306, which in turn includes outer threads formed thereon that mate with the threads formed on the inner surface of the U-shaped head 302a. This allows the second engagement mechanism 306 to be threaded into the U-shaped head 302a to secure the spinal fixation element 314 within the head 302a, yet to allow slidably movement of the spinal fixation element 314. The fixation element 314 can subsequently be locked within the head 302a by threading the first inner engagement mechanism 304 into the second inner engagement mechanism 306, thereby causing the distal portion 304b of the first inner engagement mechanism 304 to extend into the spinal fixation element 314. A person skilled in the art will appreciate that, while threads are shown for mating the engagement mechanisms to the anchoring element, virtually any mating technique can be used including, for example, a twist-lock, a dovetail, a snap-fit, etc.

Figure 7A:
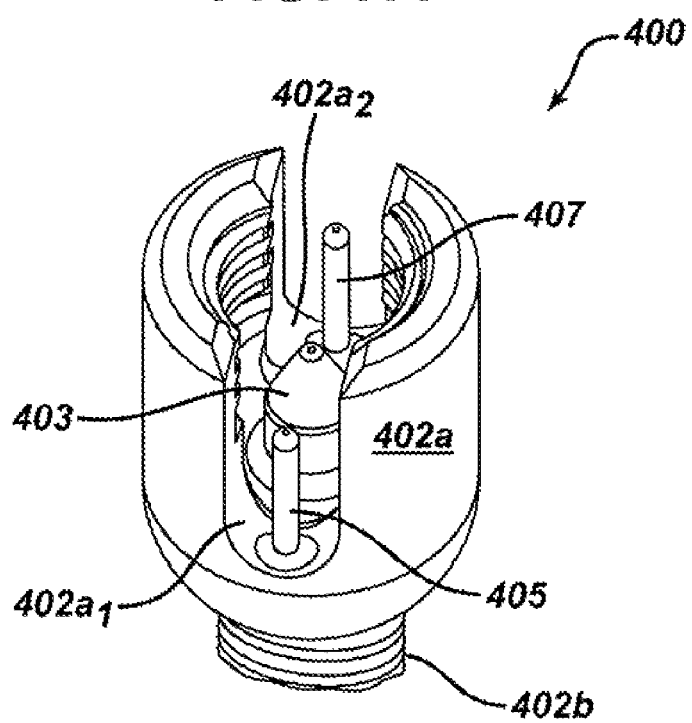
FIG. 7A is a top perspective view of a portion of a spinal anchoring device having several protrusions formed thereon in accordance with yet another embodiment of the present invention.
Figure 7B:
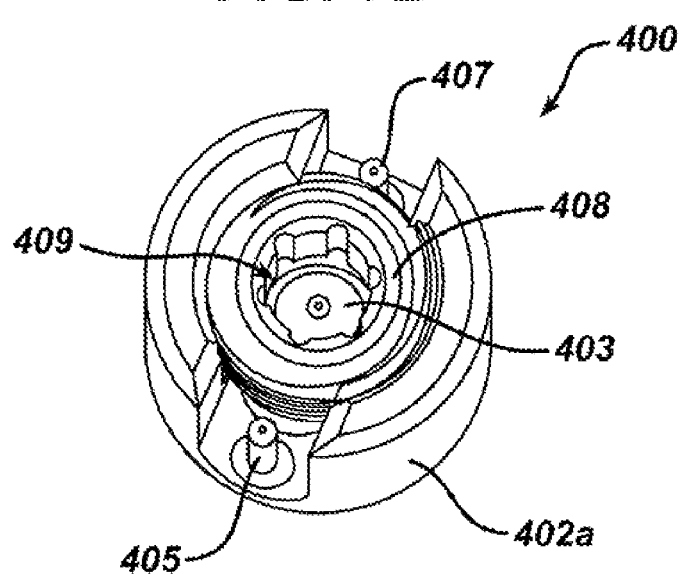
FIG. 7B is a top view of the spinal anchoring element shown in FIG. 7A with a locking mechanism disposed therein.

The spinal anchoring devices can also include a variety of other features to prevent slidable movement of a fixation element relative thereto. Suitable engagement features include, for example, protrusions, such as those described with respect to FIGS. 2A-2B, knurling on the surface of each recess, non-slip coatings, and other features known in the art. FIGS. 7A and 7B illustrate yet another embodiment of a spinal anchoring device 400 having three protrusions formed thereon that are adapted to prevent slidable movement of a fixation element relative thereto. In particular, the spinal anchoring device 400, which is similar to anchoring device 100 shown in FIG. 4A, includes a central protrusion 403 extending proximally from a substantial mid-portion of the U-shaped head 402a, and first and second smaller protrusions 405, 407 extending proximally from the recesses $402a_1$, $402a_2$ formed in the U-shaped head 402a. Each of the protrusions 403, 405, 407 is adapted to extend into a spinal fixation element (not shown) seated within the head 402a of the anchoring element 402. The spinal fixation element can then be locked within the head 402a using an engagement mechanism. As shown in FIG. 7B, the engagement mechanism 408 is threaded for mating with corresponding threads formed on the inner surface of the U-shaped head 402a. The engagement mechanism 408 also includes a central lumen 409 extending therethrough for receiving at least a portion of the central protrusion 403.

Figure 8A:
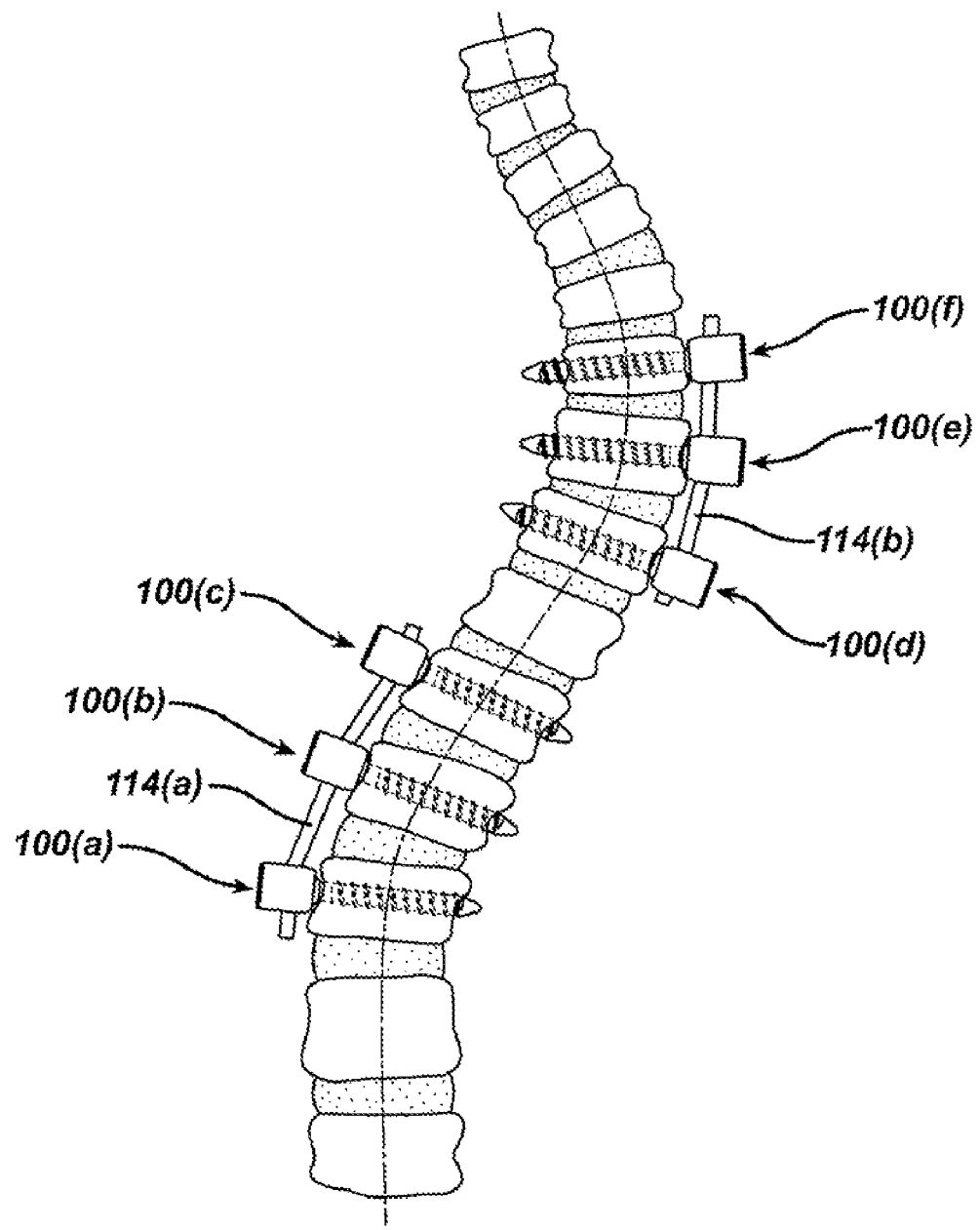
FIG. 8A is a perspective view of a deformed human spinal column having multiple spinal anchoring devices, as shown in FIGS. 4A-4C, implanted therein and mated to one another by first and second spinal fixation elements in accordance with another embodiment of the present invention.
Figure 8B:
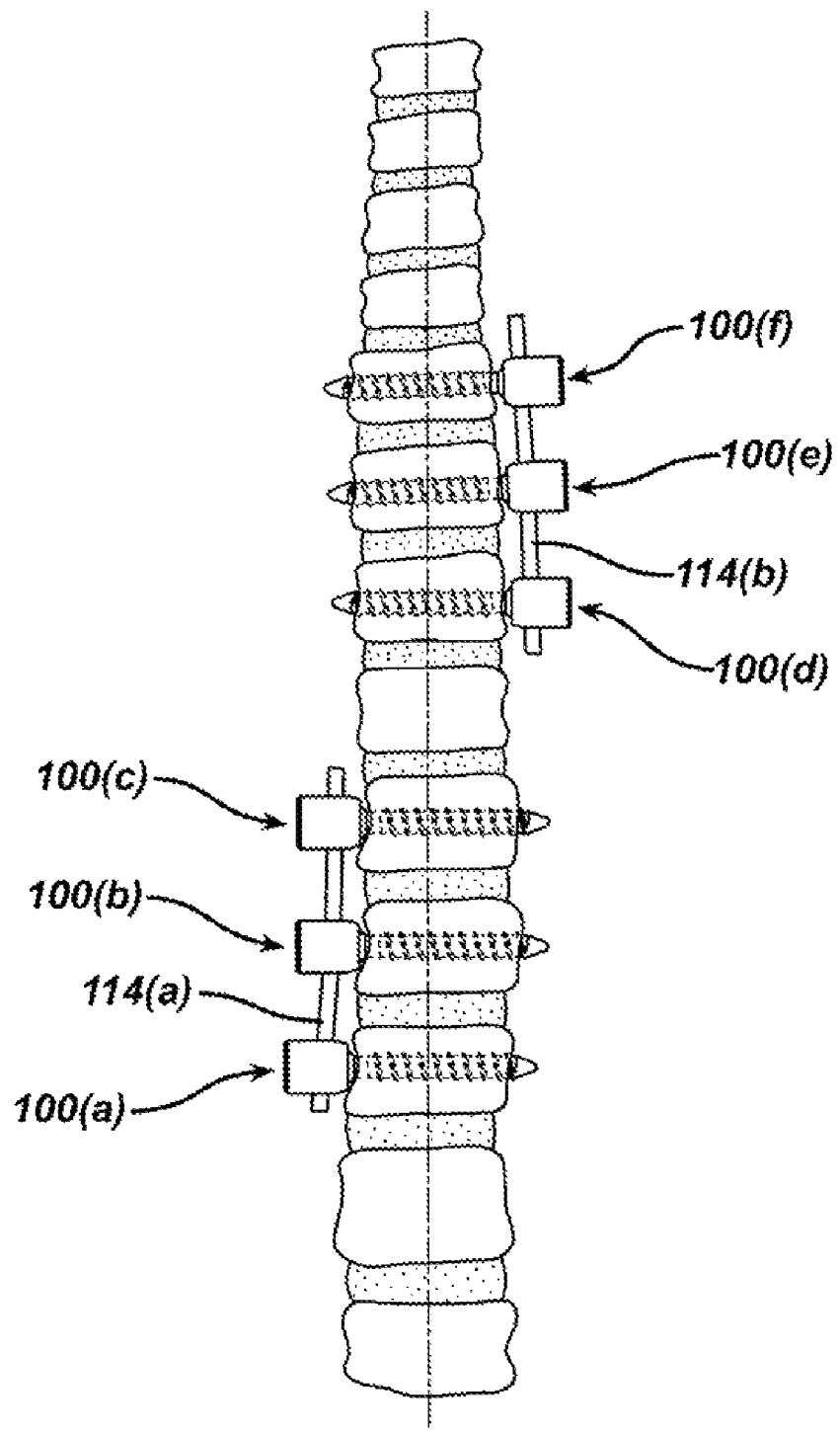
FIG. 8B is a perspective view of the human spinal column shown in FIG. 8A after the deformity is corrected.

FIGS. 8A-8B illustrate one exemplary method for correcting spinal deformities using a spinal anchoring device, such as device 100 shown in FIGS. 4A-4D. In FIG. 8A, a human spinal column having a right thoraco-lumbar scoliotic deformity is shown, however the methods can be used to correct a variety of spinal deformities. Following standard surgical procedures, the antero-lateral aspect of the thoraco-lumbar spinal vertebrae are exposed. In order to induce correction at each spinal level, several spinal anchoring elements 100(a)-(f) are implanted in one or more adjacent vertebrae, as shown. Radiographs may be obtained to determine the corrective actions needed, and thus to determine the proper placement for each anchoring element 100(a)-(f). As shown in FIG. 8A, three anchors 100(a), 100(b), 100(c) are placed in the sagittal plane on the concave side of the curve in the spinal column, and three additional anchors 100(d), 100(e), 100(f) are placed on the opposed convex side of the spinal column at a higher level than the first three anchors 100(a), 100(b), 100(c).

Next, a first fixation element 114(*a*) is positioned within spinal anchoring devices 100(*a*), 100(*b*), 100(*c*), and a second fixation element 114(*b*) is positioned within spinal anchoring devices 100(*d*), 100(*e*), 100(*f*). An engagement mechanism can then be at least partially applied to each anchoring device 100(*a*)-(*f*) to at least temporarily retain the fixation element 114(*a*), 114(*b*) therein, and preferably at least one of the engagement mechanisms on each side of the spine is fully tightened to lock the first and second fixation elements 114(*a*), 114(*b*) to one of the anchoring devices, e.g., devices 100(*a*) and 100(*d*). The fixation elements 114(*a*), 114(*b*) can then be selectively tensioned between each anchoring device 100(*a*)-(*f*) by tightening the engagement mechanism at each level. The tension between each vertebra can vary depending on the desired correction, which can be accomplished intraoperatively by tensioning the fixation elements 114(*a*), 114(*b*) to achieve the correction immediately, and/or by allowing normal growth of the spine to achieve correction by asymmetrically restricting growth using the fixation elements 114(*a*), 114(*b*). FIG. 8B illustrates the spinal column of FIG. 8A with the deformity corrected. Once correction has been achieved, the fixation elements can optionally be cut to release the tension at one or more levels. In one embodiment, the fixation elements can be cut in a minimally invasive procedure. Cutting the fixation elements is particularly advantageous to prevent over-correction.

Figure 9:
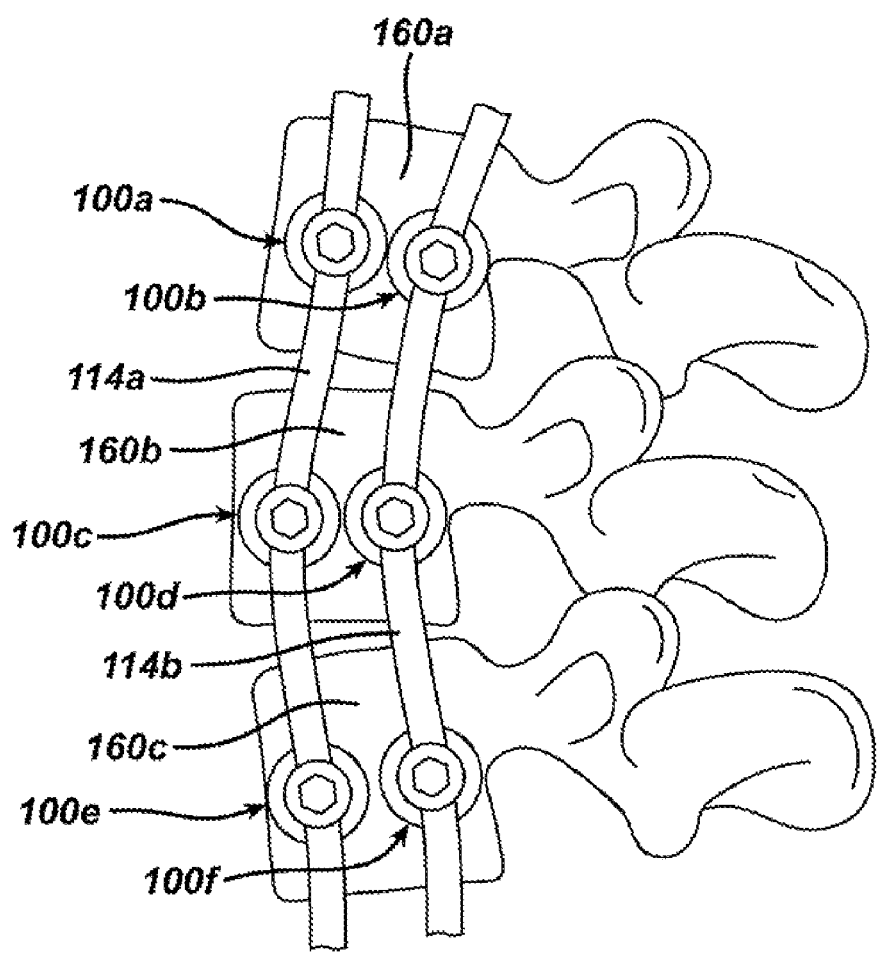
FIG. 9 is a perspective view of a portion of a deformed human spinal column having multiple spinal anchoring devices, as shown in FIGS. 4A-4C, implanted therein in accordance with yet another embodiment of the present invention.

As noted above, the position of each fixation element along the patient's spinal column will vary depending on the spinal deformity being corrected. By way of non-limiting example, as shown in FIG. 9, to achieve correction of a scoliotic deformity in the frontal plane, both fixation elements 114*a*, 114*b* can be placed on the convex side of the curve, with one posterior fixation element 114*b* and one anterior fixation element 114*a*. The fixation elements 114*a*, 114*b* are mated to the vertebrae by several spinal fixation devices 100*a*, 100*b*, 100*c*, 100*d*, 100*e*, 100*f* that are implanted adjacent to one another within each of several adjacent vertebrae (only three vertebrae 160*a*, 160*b*, 160*c* are shown for illustration purposes). Spinal fixation devices 100*a*, 100*c*, and 100*e* are positioned on the anterior side of the vertebrae, and spinal fixation devices 100*b*, 100*d*, and 100*f* are positioned on the posterior side of the vertebrae. Tension can then be applied to both the anterior and posterior fixation elements 114*a*, 114*b* by selectively fastening the fixation devices 100*a*, 100*b*, 100*c*, 100*d*, 100*e*, 100*f* to lock the fixation elements 114*a*, 114*b* therein. To correct only the frontal plane deformity, equal tension is preferably applied to both fixation elements 114*a*, 114*b*, and the degree of tension dictates how much correction is achieved intraoperatively and how much is left to take place during asymmetric growth restriction.

To achieve correction of a saggittal plane deformity in addition to correction of a scoliotic deformity, the anterior and posterior fixation elements 114*a*, 114*b* are preferably tensioned differently. To increase lordosis, the posterior fixation element 114*b* is tightened more than the anterior fixation element 114*a*. To increase kyphosis, the anterior fixation element 114*a* is tightened more than the posterior fixation element 114*b*. Similar to correcting the scoliotic deformity, the degree of tension dictates how much correction is achieved intraoperatively and how much is left to take place during asymmetric growth restriction.

Figure 10A:
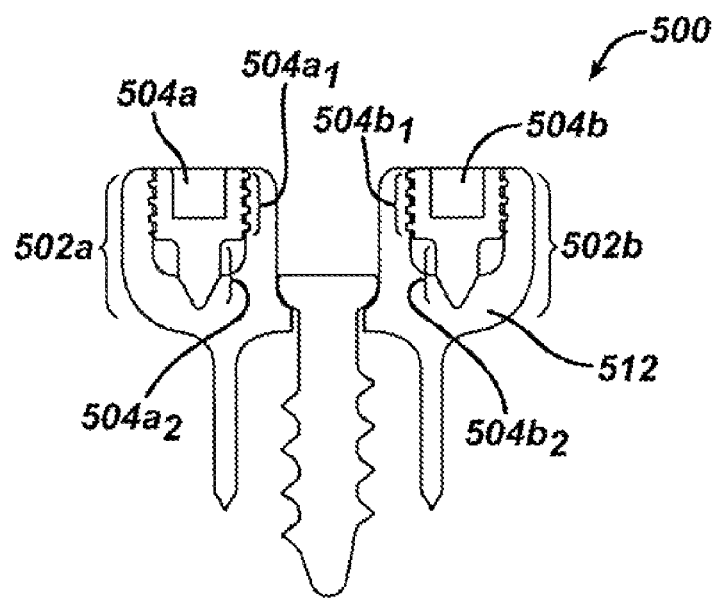
FIG. 10A is a side perspective view of yet another embodiment of a spinal anchoring device in accordance with the present invention.
Figure 10B:
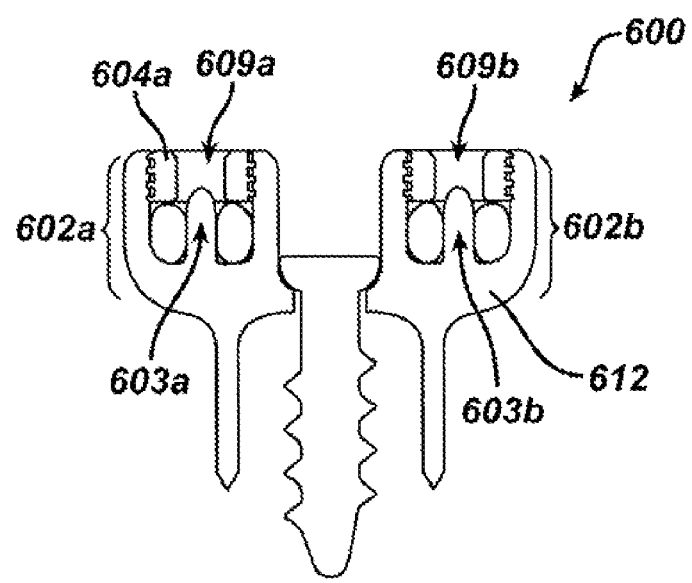
FIG. 10B is a side perspective view of a spinal anchoring device in accordance with yet another embodiment of the present invention.

FIGS. 10A-10B illustrate additional embodiments of spinal anchoring devices 500, 600. In these embodiments, the anchoring devices 500, 600 include a combination of features from anchoring device 10, shown in FIG. 1, and from anchoring device 100 shown in FIG. 4. In particular, each anchoring device 500 includes a spinal anchoring element 512, 612 that is similar to spinal anchoring element 12 shown in FIG. 1. Anchoring elements 512, 612, however, include first and second U-shaped heads 502*a*, 502*b*, 602*a*, 602*b* formed thereon for seating first and second fixation elements. The heads 502*a*, 502*b*, 602*a*, 602*b*, which are similar to head 102 in FIG. 4, allow separate engagement mechanisms 504*a*, 504*b*, 506*a*, 506*b* to be applied thereto to secure the fixation elements separately within the heads 502*a*, 502*b*, 602*a*, 602*b*. In FIG. 10A, the engagement mechanisms 504*a*, 504*b* are similar to engagement mechanism 104 in that they include a proximal portion $504a_1$, $504b_1$ that mates to an internal portion of the U-shaped head 502*a*, 502*b*, and a distal portion $504a_2$, $504b_2$ that is adapted to extend into a spinal fixation element to prevent slidably movement of the fixation element relative to the anchoring element 512. In FIG. 10B, the engagement mechanisms 604*a*, 604*b* are similar to engagement mechanism 408 shown in FIGS. 8A and 8B in that they each include a central lumen 609*a*, 609*b* for receiving a portion of a protrusion 603*a*, 603*b* formed within the U-shaped head 602*a*, 602*b*, and they are each adapted to threadably mate with an inner surface of each U-shaped head 602*a*, 602*b*.

In use, the separate engagement mechanisms 504*a*, 504*b*, 604*a*, 604*b* on each device 500, 600 allow first and second fixation elements disposed within the anchoring elements 512, 612 to be individually tensioned and locked relative to the anchoring element 512, 612, thereby allowing segmental tension to be created between adjacent vertebrae.

The following example serves to further illustrate the invention:

EXAMPLE 1

A 3 mm Ultra-High Molecular Weight Polyethylene (Spectra) cable was attached to a U-shaped head of a bone screw using a set screw tightened with a torque of 5 N-m. The set screw did not include anything that penetrated into the cable. A second 3 mm Ultra-High Molecular Weight Polyethylene (Spectra) cable was attached to a U-shaped head of a bone screw using an engagement mechanism having a pin that was inserted through the cable. The engagement mechanism was tightened with a torque of 3 N-m. The force required to move each cable was tested. The cable tightened with the set screw required 32 N of force to cause 3 mm of slippage, whereas the cable tightened using the engagement mechanism required 244 N of force to cause 3 mm of slippage. Accordingly, the engagement mechanism with the pin that extended through the cable required 750% more force to move the cable.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A device for treating spinal deformities, comprising:
a spinal anchoring element adapted to seat first and second spinal fixation elements at a distance spaced apart from one another, the spinal anchoring element having a bore extending therethrough;
a polyaxial fastening element adapted to extend distally through the bore to mate the spinal anchoring element to bone the fastening element being adapted to move polyaxially relative the spinal anchoring element when the fastening element extends distally through the bore;

a closure mechanism adapted to removably mate to the spinal anchoring element to lock each of the first and second spinal fixation elements in a fixed position relative to the spinal anchoring element, the closure mechanism having a tapered bore extending therethrough that axially aligns with the bore in the spinal anchoring element when the closure mechanism is mated to the spinal anchoring element; and a set screw having a head that is received within the tapered bore in the closure mechanism, and a threaded shaft adapted to threadably engage threads in the bore in the spinal anchoring element to mate the closure mechanism to the spinal anchoring element, wherein the set screw is configured to prevent polyaxial movement of the fastening element relative to the spinal anchoring element when the set screw is fully threaded into the bore.

2. The device of claim 1, wherein the spinal anchoring element includes a first recess adapted to receive a first spinal fixation element, and a second recess spaced a distance apart from the first recess and adapted to receive a second spinal fixation element.

3. The device of claim 2, wherein the spinal anchoring element includes a central portion positioned between the first and second recesses and adapted to receive the fastening element for mating the anchoring element to bone.

4. The device of claim 3, wherein the central portion includes the bore extending therethrough.

5. The device of claim 4, wherein the closure mechanism includes a central portion adapted to receive the set screw for mating the closure mechanism to the spinal anchoring element.

6. The device of claim 1, wherein the fastening element comprises a bone screw.

7. The device of claim 3, wherein the first recess is formed in a first end portion of the spinal anchoring element and the second recess is formed in a second, opposed end portion of the spinal anchoring element.

8. The device of claim 7, wherein each end portion includes a superior surface and an inferior surface, the first and second recesses being formed in the superior surface.

9. The device of claim 8, further comprising a bone engaging member extending distally from the inferior surface of each of the first and second end portions.

10. The device of claim 9, wherein each bone engaging member comprises a spike adapted to extend into bone to prevent rotation of the spinal anchoring element.

11. The device of claim 7, wherein the closure mechanism includes a first end portion adapted to lock a spinal fixation element within the first recess, and a second end portion adapted to lock a spinal fixation element within the second recess.

12. The device of claim 11, wherein the first and second end portions on the closure mechanism each include a bore formed therethrough for receiving an engagement mechanism adapted to extend into and engage a spinal fixation element disposed within each of the first and second recesses in the spinal anchoring element.

13. The device of claim 12, further comprising first and second engagement mechanisms, each engagement mechanism including a proximal, threaded portion adapted to mate with corresponding threads formed within the bore in the closure mechanism, and a distal pin member adapted to extend into a spinal fixation element positioned in each of the first and second recesses.

14. The device of claim 1, further comprising first and second spinal fixation elements adapted to be disposed between the spinal anchoring element and the closure mechanism.

15. The device of claim 14, wherein each spinal fixation element comprises a flexible fixation element.

16. The device of claim 14, wherein each spinal fixation element is formed from a bioabsorbable material.

17. The device of claim 2, wherein each recess has a substantially concave shape.

18. The device of claim 2, wherein each recess includes at least one protrusion formed therein and adapted to extend into and engage a spinal fixation element positioned therein.

19. The device of claim 2, wherein the closure mechanism includes at least one protrusion formed thereon and adapted to extend into and engage a spinal fixation element disposed in each of the first and second recesses formed in the spinal anchoring element.

20. The device of claim 1, wherein a distal terminal end of the set screw contacts a proximal terminal end of the fastening element to prevent polyaxial movement of the fastening element relative to the spinal anchoring element when the set screw is fully threaded into the bore.

* * * * *